(12) United States Patent
Zia et al.

(10) Patent No.: US 11,827,760 B2
(45) Date of Patent: Nov. 28, 2023

(54) POLYESTER POLYMER COMPOSITIONS

(71) Applicant: Celanese Sales Germany GmbH, Taunus (DE)

(72) Inventors: Qamer Zia, Raunheim (DE); Kirsten Markgraf, Weinheim (DE); Dirk Zierer, Hattersheim (DE)

(73) Assignee: Celanese Sales Germany GmbH, Taunus (DE)

( * ) Notice: Subject to any disclaimer, the term of this patent is extended or adjusted under 35 U.S.C. 154(b) by 0 days.

(21) Appl. No.: 17/575,990

(22) Filed: Jan. 14, 2022

(65) Prior Publication Data

US 2022/0135751 A1 May 5, 2022

Related U.S. Application Data

(63) Continuation of application No. 15/915,350, filed on Mar. 8, 2018, now Pat. No. 11,225,559.

(60) Provisional application No. 62/469,874, filed on Mar. 10, 2017.

(51) Int. Cl.
| | |
|---|---|
| *C08J 5/04* | (2006.01) |
| *C08L 67/02* | (2006.01) |
| *A61M 15/00* | (2006.01) |
| *A61M 5/31* | (2006.01) |
| *C08L 27/18* | (2006.01) |
| *C08L 67/03* | (2006.01) |

(Continued)

(52) U.S. Cl.
CPC .............. *C08J 5/043* (2013.01); *A61M 5/31* (2013.01); *A61M 15/0001* (2014.02); *C08L 27/18* (2013.01); *C08L 67/02* (2013.01); *C08L 67/03* (2013.01); *C08L 69/005* (2013.01); *C08L 83/04* (2013.01); *A61M 2205/0222* (2013.01); *C08J 2367/00* (2013.01); *C08J 2383/04* (2013.01); *C08L 2203/02* (2013.01); *C08L 2205/03* (2013.01)

(58) Field of Classification Search
None
See application file for complete search history.

(56) References Cited

U.S. PATENT DOCUMENTS

| | | |
|---|---|---|
| 3,629,310 A | 12/1971 | Bailey et al. |
| 4,111,887 A | 9/1978 | Shaner et al. |
| 4,394,468 A | 7/1983 | Lu |

(Continued)

FOREIGN PATENT DOCUMENTS

| | | |
|---|---|---|
| CN | 101343396 A | 1/2009 |
| CN | 101759955 A | 6/2010 |

(Continued)

OTHER PUBLICATIONS

Dow Corning® Si Powder Resin Modifiers, Product Information Sheet, 2017.

(Continued)

*Primary Examiner* — Tae H Yoon
(74) *Attorney, Agent, or Firm* — Dority & Manning, P.A.

(57) ABSTRACT

A fiber reinforced polyester polymer composition is disclosed that contains at least one tribological modifier. The tribological modifier may comprise an ultra-high molecular weight silicone alone or in combination with polyytetrafluoroethylene particles. The composition not only has excellent tensile properties but also can produce a low friction surface.

15 Claims, 1 Drawing Sheet

(51) Int. Cl.
*C08L 69/00* (2006.01)
*C08L 83/04* (2006.01)

(56) References Cited

U.S. PATENT DOCUMENTS

| | | | |
|---|---|---|---|
| 4,436,200 A | 3/1984 | Hodlewsky et al. | |
| 4,480,017 A | 10/1984 | Takeuchi et al. | |
| 4,645,785 A | 2/1987 | Heinz et al. | |
| 4,874,807 A | 10/1989 | Endo et al. | |
| 4,879,331 A | 11/1989 | Endo et al. | |
| 4,959,404 A | 9/1990 | Nakane et al. | |
| 5,063,263 A | 11/1991 | Hayes et al. | |
| 5,177,123 A | 1/1993 | Takayama et al. | |
| 5,237,008 A | 8/1993 | Kosinski | |
| 5,264,516 A | 11/1993 | Hijikata et al. | |
| 5,298,537 A | 3/1994 | Vaidya | |
| 5,309,705 A | 5/1994 | Takahashi et al. | |
| 5,310,822 A | 5/1994 | Kielhorn-Bayer et al. | |
| 5,314,912 A | 5/1994 | Yoshitani et al. | |
| 5,346,737 A | 9/1994 | Takahashi et al. | |
| 5,374,485 A | 12/1994 | Wakatsuka et al. | |
| 5,415,791 A | 5/1995 | Chou et al. | |
| 5,482,987 A | 1/1996 | Forschirm | |
| 5,530,061 A | 6/1996 | Sanada et al. | |
| 5,538,793 A | 7/1996 | Inokuchi et al. | |
| 5,559,180 A | 9/1996 | Takahashi et al. | |
| 5,616,680 A | 4/1997 | Linstid, III et al. | |
| 5,641,824 A | 6/1997 | Forschirm | |
| 5,679,733 A | 10/1997 | Malik et al. | |
| 5,704,613 A | 1/1998 | Holtkamp | |
| 5,759,642 A | 6/1998 | Berger | |
| 5,824,742 A | 10/1998 | Shinohara | |
| 5,852,135 A | 12/1998 | Kanai et al. | |
| 5,854,324 A | 12/1998 | Tajima et al. | |
| 5,886,066 A | 3/1999 | Forschirm | |
| 5,889,102 A | 3/1999 | Haack et al. | |
| 6,046,141 A | 4/2000 | Kurz et al. | |
| 6,114,492 A | 9/2000 | Linstid, III et al. | |
| 6,130,280 A | 10/2000 | Yokoyama et al. | |
| 6,161,685 A | 12/2000 | Stebnicki | |
| 6,191,222 B1 | 2/2001 | Keller et al. | |
| 6,207,769 B1 | 3/2001 | Gerlach et al. | |
| 6,284,828 B1 | 9/2001 | Takayama | |
| 6,360,881 B2 | 3/2002 | Stebnicki et al. | |
| 6,414,155 B1 | 7/2002 | Sassi et al. | |
| 6,489,388 B1 | 12/2002 | Kurz et al. | |
| 6,514,611 B1 | 2/2003 | Shepherd et al. | |
| 6,569,931 B2 | 5/2003 | Furukawa et al. | |
| 6,602,953 B1 | 8/2003 | Horio et al. | |
| 6,790,385 B2 | 9/2004 | Schleith et al. | |
| 6,821,630 B2 | 11/2004 | Takada et al. | |
| 6,852,677 B2 | 2/2005 | Kurz et al. | |
| 7,056,965 B2 | 6/2006 | Seyama et al. | |
| 7,067,182 B2 | 6/2006 | Li et al. | |
| 7,247,665 B1 | 7/2007 | Woerner et al. | |
| 7,256,966 B2 | 8/2007 | Horio et al. | |
| 7,396,492 B2 | 7/2008 | Price et al. | |
| 7,638,565 B2 | 12/2009 | Harashina | |
| 7,645,821 B2 | 1/2010 | Disch et al. | |
| 7,821,740 B2 | 10/2010 | Horio et al. | |
| 7,851,585 B2 | 12/2010 | Brison et al. | |
| 7,893,140 B2 | 2/2011 | Hase | |
| 8,058,330 B2 | 11/2011 | Irie et al. | |
| 8,097,670 B2 | 1/2012 | Nagai et al. | |
| 8,101,042 B2 | 1/2012 | Gantner et al. | |
| 8,829,085 B2 | 9/2014 | Markgraf et al. | |
| 8,865,805 B2 | 10/2014 | Markgraf et al. | |
| 9,062,183 B2 | 6/2015 | Markgraf et al. | |
| 9,187,634 B2 | 11/2015 | Sivebaek | |
| 9,296,894 B2 | 3/2016 | Wang et al. | |
| 9,303,145 B2 | 4/2016 | Markgraf et al. | |
| 9,422,428 B2 | 8/2016 | Kaushik et al. | |
| 9,540,553 B2 | 1/2017 | Markgraf et al. | |
| 9,790,363 B2 | 10/2017 | Chen et al. | |
| 10,030,208 B2 | 7/2018 | Zia et al. | |
| 10,047,697 B2 * | 8/2018 | Kojima | F16J 15/0818 |
| 10,093,069 B2 * | 10/2018 | Liu | F16J 15/027 |
| 10,479,954 B2 | 11/2019 | Zia et al. | |
| 11,225,559 B2 * | 1/2022 | Zia | C08L 83/04 |
| 2003/0039834 A1 | 2/2003 | Gunn | |
| 2003/0195280 A1 | 10/2003 | Disch et al. | |
| 2004/0135118 A1 | 7/2004 | Waggoner | |
| 2004/0158005 A1 | 8/2004 | Bloom | |
| 2005/0003721 A1 | 1/2005 | Greulich et al. | |
| 2005/0043492 A1 | 2/2005 | Chin et al. | |
| 2005/0107513 A1 | 5/2005 | Papke | |
| 2005/0167071 A1 | 8/2005 | Kendall, Sr. et al. | |
| 2006/0025507 A1 | 2/2006 | Moore et al. | |
| 2007/0032605 A1 | 2/2007 | Harashina | |
| 2007/0066746 A1 | 3/2007 | Gunnewig et al. | |
| 2007/0202332 A1 | 8/2007 | Gunnewig et al. | |
| 2008/0234413 A1 | 9/2008 | Shinohara et al. | |
| 2009/0283931 A1 | 11/2009 | Pfeiffer et al. | |
| 2010/0022691 A1 | 1/2010 | Katsuchi et al. | |
| 2010/0093901 A1 | 4/2010 | Kawaguchi et al. | |
| 2012/0029137 A1 | 2/2012 | Jian et al. | |
| 2012/0129976 A1 | 5/2012 | Ratnagiri | |
| 2012/0276314 A1 | 11/2012 | Latz et al. | |
| 2013/0331488 A1 | 12/2013 | Markgraf et al. | |
| 2014/0080951 A1 | 3/2014 | Raman et al. | |
| 2014/0167088 A1 | 6/2014 | Lu | |
| 2014/0316041 A1 | 10/2014 | Mehta | |
| 2015/0065654 A1 | 3/2015 | Markgraf et al. | |
| 2015/0111794 A1 | 4/2015 | Zia et al. | |
| 2015/0111796 A1 | 4/2015 | Zia et al. | |
| 2015/0175787 A1 | 6/2015 | Zia et al. | |
| 2015/0175928 A1 | 6/2015 | Zia et al. | |
| 2015/0274930 A1 | 10/2015 | Jon et al. | |
| 2015/0299458 A1 | 10/2015 | Kaushik et al. | |
| 2015/0353732 A1 | 12/2015 | Wang | |
| 2016/0177219 A1 | 6/2016 | Markgraf et al. | |

FOREIGN PATENT DOCUMENTS

| | | | |
|---|---|---|---|
| CN | 104419141 A | | 3/2015 |
| CN | 106567155 A | * | 4/2017 |
| DE | 102004057190 A1 | | 6/2006 |
| DE | 102008055840 A1 | | 5/2010 |
| EP | 1630198 A1 | | 3/2006 |
| EP | 2532905 A1 | | 12/2012 |
| EP | 2653497 A1 | | 10/2013 |
| EP | 2712836 A1 | | 4/2014 |
| GB | 1331829 A | | 9/1973 |
| GB | 2537756 A | | 10/2016 |
| JP | H 01126359 A | | 5/1989 |
| JP | H 01204950 A | | 8/1989 |
| JP | H 04234450 A | | 8/1992 |
| JP | H 05295230 A | | 11/1993 |
| JP | H 0867798 A | | 3/1996 |
| JP | H 08311351 A | | 11/1996 |
| JP | H 11181231 A | | 7/1999 |
| JP | H 11181232 A | | 7/1999 |
| JP | 2000109702 A | | 4/2000 |
| JP | 3081610 B1 | | 8/2000 |
| JP | 2009050985 A | | 3/2009 |
| WO | WO 2005/059030 A1 | | 6/2005 |
| WO | WO 2010/073529 A1 | | 7/2010 |
| WO | WO 2016/098026 A1 | | 6/2016 |

OTHER PUBLICATIONS

Laursen J L et al; "Influence of tribological additives on friction and impact performance of injection moulded polyacetal", Wear, Elsevier Sequoia, Lausanne, CH, vol. 267, No. 12, Dec. 1, 2009, pp. 2294-2302, XP026751088.
Tekuma Kunststoff GMBH, Kepital TS-25H data sheet, 1 page, www.tekuma.de.
Mas Rusplast, Our solutions. Polyacetal Kepital: wear-resistant friction units, machine translation, Sep. 6, 2013, 1 page.
Ticona GMBH GUR Ultra-high Molecular Weight Polyethylene (PE-UHMW) Published Mar. 2001, pp. 1-35.
The International Search Report and The Written Opinion Of The

(56) References Cited

OTHER PUBLICATIONS

International Searching Authority Corresponding to Application No. PCT/IB2018/051513 dated May 23, 2018.

* cited by examiner

POLYESTER POLYMER COMPOSITIONS

RELATED APPLICATIONS

The present application is a continuation application and is based upon and claims priority to U.S. patent application Ser. No. 15/915,350, filed on Mar. 8, 2018, now U.S. Pat. No. 11,225,559, which claims priority to U.S. Provisional Patent Application Ser. No. 62/469,874, filed on Mar. 10, 2017, which are both incorporated herein by reference in their entirety.

BACKGROUND

Engineering thermoplastics and elastomeric materials are often used in numerous and diverse applications in order to produce molded parts and products. For instance, polyester polymers and polyester elastomers are used to produce all different types of molded products, such as injection molded products, blow molded products, and the like. Polyester polymers, for instance, can be formulated in order to be chemically resistant, to have excellent strength properties and, when formulating compositions containing polyester elastomers, to be flexible. Of particular advantage, polyester polymers can be melt processed due to their thermoplastic nature. In addition, polyester polymers can be recycled and reprocessed.

In certain applications, thermoplastic polymers, such as polyester polymers, are combined with fibrous fillers in order to increase the modulus and/or tensile strength of parts and products made from the reinforced composition. Problems have been experienced in the past, however, in incorporating reinforcing fibers into a polyester polymer matrix that has the desired balance of properties. For instance, polyester polymer composites containing reinforcing fibers may have adequate strength properties but can experience an increase in surface friction when moved across an adjacent surface. The increase in friction, for instance, can cause abrasive wear after extended periods of use. These problems can become exacerbated when a first part made from the polyester polymer matrix is designed to slide or rub against an adjacent part made from the same reinforced polyester matrix.

In view of the above, a need currently exists for reinforced polyester polymer compositions that can be formulated so as to have a desired balance of physical properties and characteristics. More particularly, a need exists for a fiber reinforced polyester polymer composition that also has reduced friction properties.

SUMMARY

The present disclosure is generally directed to a polyester polymer composition containing reinforcing fibers for increasing tensile strength in combination with a tribological additive package that has been found to dramatically decrease the coefficient of friction characteristics of articles molded from the composition. Parts and articles can be made in accordance with the present disclosure that not only have excellent strength characteristics and properties but that also are well suited for use in applications where the parts or articles are intended to slide against an opposing surface. For instance, the articles and products can be formulated so as to produce no audible noise when sliding against an opposing component or part, especially when the opposing component or part is also made from the same or a similar polymer composition.

In one embodiment, for instance, the polymer composition of the present disclosure comprises a polyester polymer comprising a polybutylene terephthalate polymer. The polybutylene terephthalate polymer can be present alone or in combination with other polymers within the composition. The other polymers may comprise, for instance, a different polyester polymer such as polyethylene terephthalate, a polycarbonate polymer, and the like. The polymer composition also contains reinforcing fibers, such as glass fibers. The reinforcing fibers can be present in the composition generally in an amount greater than about 5% by weight, such as in an amount greater than about 10% by weight, such as in an amount greater than about 15% by weight. The reinforcing fibers are generally present in an amount less than about 55% by weight, such as in an amount less than about 45% by weight, such as in an amount less than about 35% by weight.

In accordance with the present disclosure, the polymer composition further contains at least one tribological modifier. The tribological modifier, in one embodiment, can comprise an ultra-high molecular weight silicone. The ultra-high molecular weight silicone can have a kinematic viscosity of greater than about 100,000 $mm^2s^{-1}$. For example, the ultra-high molecular weight silicone can be present in the polymer composition in an amount from about 0.1% to about 10% by weight, such as from about 0.5% to about 3% by weight. In one embodiment, the ultra-high molecular weight silicone comprises a polydimethylsiloxane.

In an alternative embodiment, the tribological modifier contained within the polymer composition may comprise a polytetrafluoroethylene polymer. The polytetrafluoroethylene polymer may be present alone or in combination with an ultra-high molecular weight silicone.

In one particular embodiment, the polymer composition comprises a polybutylene terephthalate polymer in an amount from about 50% to about 90% by weight, reinforcing fibers such as glass fibers being present in the composition in an amount from about 5% to about 30% by weight, an ultra-high molecular weight silicone being present in the composition in an amount from about 0.5% to about 4% by weight and a polytetrafluoroethylene polymer being present in the composition in an amount from about 1% to about 20% by weight.

As described above, the polymer composition can be formulated to have low friction properties. For instance, the polymer composition can exhibit a dynamic coefficient of friction according to VDA 230-206 of less than about 0.08 when tested against polycarbonate containing 15% by weight polytetrafluoroethylene and 20% by weight glass fiber or when tested against polybutylene terephthalate containing 15% by weight polytetrafluoroethylene and 20% by weight glass fiber, or when tested against itself at a speed of 8 mm/s, at a load of 30 N and after 1,000 cycles. In one embodiment, the polymer composition may exhibit a dynamic coefficient of friction of less than about 0.07, such as less than about 0.05 when tested against the above materials.

When an ultra-high molecular weight silicone is present in the composition, the silicone can be added with a carrier. In one embodiment, for instance, the ultra-high molecular weight silicone can be grafted to silica and added to the composition. Alternatively, the ultra-high molecular weight silicone may be combined with a carrier polymer prior to being blended with the other components. The carrier polymer, for instance, may comprise a polycarbonate polymer or a polyester polymer. The polyester polymer, for instance, may comprise polyethylene terephthalate, a copolyester, and/or a polyester elastomer.

In one embodiment, the polymer composition of the present disclosure is formulated for producing medical products. When producing medical products, for instance, the polymer composition can be formulated to be isocyanate-free.

In one embodiment, the polymer composition can be used to produce medical inhalers, injectors, and the like. The medical product, for instance, may include a first sliding member in operative association with a second sliding member. The first sliding member and the second sliding member may be positioned to remain in contact and move relative to each other. At least one of the sliding members can be made from the polymer composition of the present disclosure. In one embodiment, for instance, both sliding members are made from the polymer composition of the present disclosure.

Other features and aspects of the present disclosure are discussed in greater detail below.

BRIEF DESCRIPTION OF THE DRAWINGS

A full and enabling disclosure of the present disclosure is set forth more particularly in the remainder of the specification, including reference to the accompanying figures, in which.

Figure 1:
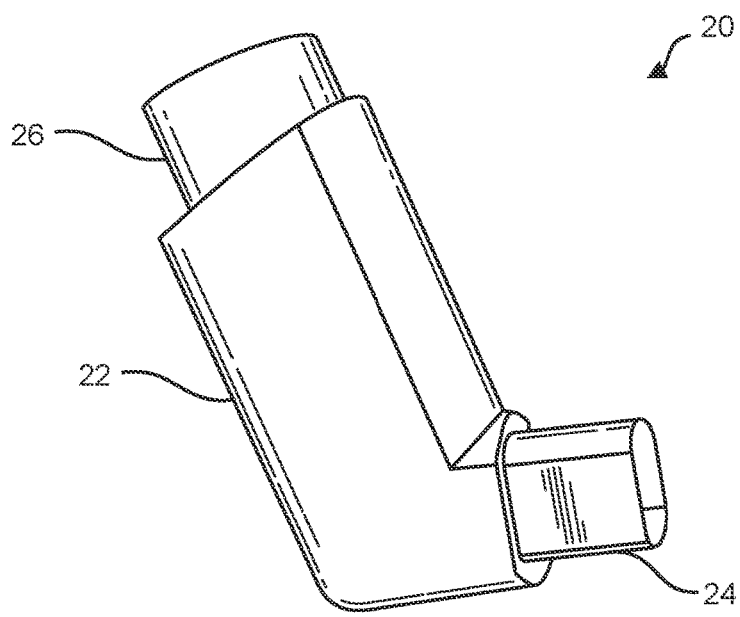
FIG. 1 is a perspective view of a medical inhaler made in accordance with the present disclosure.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present disclosure.

In general, the present disclosure is directed to a polyester polymer composition and to polymer articles made from the composition that not only have increased strength properties but also have improved tribological properties such as low friction properties. The polyester polymer composition contains reinforcing fibers for increasing the strength of the composition. The reinforcing fibers, however, can increase the friction characteristics of the composition and cause abrasive wear when placed in use. In order to counterbalance the presence of the reinforcing fibers, the polymer composition contains a tribological stabilizer package. The tribological additive package can comprise the presence of at least one tribological modifier, such as an ultra-high molecular weight silicone, a polytetrafluoroethylene polymer, or combinations thereof.

The composition of the present disclosure can be formulated for medical applications. For example, when used in medical applications, the polymer composition can contain no isocyanates, epoxy resins, carbodiimides or other similar compounds. In certain applications, medical devices are needed in which the parts are not only made from high strength materials but that can provide ultra-low friction and reduced wear for parts that are intended to slide against an adjacent surface. As will be described in greater detail below, polymer compositions made according to the present disclosure have not only excellent strength properties but can display extremely low friction properties without the need of applying external lubricants.

When two opposing surfaces slide against each other, the surfaces react in a way that is referred to as the stick-slip phenomenon. The stick-slip phenomenon refers to the manner in which two opposing surfaces or articles slide over each other in reaction to the forces of friction. Static friction refers to the friction between two or more objects that are not moving relative to each other. Kinetic friction, on the other hand, occurs when two objects are moving relative to each other while remaining in contact. In order for one object to slide relative to another object, enough force must be exerted on one object to overcome the forces of static friction. When movement between the two objects occurs, a reduction of the friction between the two surfaces can cause a sudden increase in the velocity of movement. In other words, once one object moves relative to another object, in some applications, less force is needed to continue movement. The friction between the two surfaces can increase or decrease during movement depending upon numerous factors, including the speed at which movement continues. Stick-slip describes how surfaces alternate between sticking to each other and sliding over each other as movement occurs between two surfaces and as the conditions of movement change.

Polymer articles that have a relatively high coefficient of friction not only require greater amounts of force in order to slide one material over the other but also can be prone to wear. Over time, for instance, the materials can begin to degrade due to the forces of friction.

As two surfaces move relative to each other and the stick-slip phenomenon occurs, noise can also be generated from the two surfaces. Depending upon the stick-slip properties of the materials, noise generation can be highly audible or very quiet. In many applications, the generation of noise caused by the stick-slip phenomenon when two components are sliding against each other is highly undesirable. For instance, when designing and manufacturing medical devices and consumer products, manufacturers and engineers try to design products so that no noise generation occurs when the products are in use. Noise generation during use of the product, for instance, can create an impression with the consumer that the product is of inferior quality and made with inexpensive materials.

The present disclosure is particularly directed to a polymer composition that can be used to make molded parts such that when the parts slide against each other excessive wear and/or noise generation is inhibited and even eliminated.

For example, in one embodiment, the present disclosure is directed to a low friction assembly that includes a first sliding member in operative association with a second sliding member. The first sliding member and the second sliding member can both be made from a polymer composition formulated in accordance with the present disclosure. When tested against each other, the composition can be formulated so as to exhibit a dynamic coefficient of friction of less than about 0.08, such as less than about 0.07, such as less than about 0.06, such as less than about 0.05. The compositions or molded parts can be tested against each other according to a stick-slip test having Test No. VDA 230-206.

Specimens tested using the above method can also be analyzed to measure a wear track width which is an abrasion width. In accordance with the present disclosure, the compositions and molded articles can exhibit a wear track width of less than 0.3 mm, such as less than about 0.25 mm, such as even less than about 0.2 mm when tested at a force of 30 N and at a velocity of 8 mm/s after 1,000 cycles.

Polyester Polymer

The polymer composition of the present disclosure generally contains a polyester polymer in combination with reinforcing fibers and a tribological additive package. The polyester polymer generally comprises a polyalkylene terephthalate polymer.

Polyalkylene terephthalate polymers suitable for use herein are derived from an aliphatic or cycloaliphatic diol, or mixtures thereof, containing from 2 to about 10 carbon atoms and an aromatic dicarboxylic acid.

The polyesters which are derived from a cycloaliphatic diol and an aromatic dicarboxylic acid are prepared by condensing either the cis- or trans-isomer (or mixtures thereof) of, for example, 1,4-cyclohexanedimethanol with the aromatic dicarboxylic acid.

Examples of aromatic dicarboxylic acids include isophthalic or terephthalic acid, 1,2-di(p-carboxyphenyl)ethane, 4,4'-dicarboxydiphenyl ether, etc., and mixtures of these. All of these acids contain at least one aromatic nucleus. Fused rings can also be present such as in 1,4- or 1,5- or 2,6-naphthalene-dicarboxylic acids. In one embodiment, the dicarboxylic acid is terephthalic acid or mixtures of terephthalic and isophthalic acid.

In one embodiment, the polyalkylene terephthalate polymer present in the polymer composition comprises a polybutylene terephthalate polymer. For example, the polymer composition may contain a polybutylene terephthalate polymer in an amount greater than about 30% by weight, such as in an amount greater than about 40% by weight, such as in an amount greater than about 50% by weight, such as in an amount greater than about 60% by weight, such as in an amount greater than about 70% by weight. The polybutylene terephthalate polymer is generally present in an amount less than about 90% by weight, such as in an amount less than about 80% by weight.

The polymer composition may contain the polybutylene terephthalate polymer alone or in combination with other thermoplastic polymers. For instance, the polybutylene terephthalate polymer may be combined with other polyester polymers and/or a polycarbonate polymer. Other polyester polymers that may be present in the composition include a polyethylene terephthalate polymer or a polyethylene terephthalate copolymer. For instance, a polyethylene terephthalate copolymer or modified polyethylene terephthalate polymer can be produced with a modifying acid or a modifying diol.

As used herein, the terms "modifying acid" and "modifying diol" are meant to define compounds, which can form part of the acid and diol repeat units of a polyester, respectively, and which can modify a polyester to reduce its crystallinity or render the polyester amorphous. In one embodiment, however, the polyesters present in the polymer composition of the present disclosure are non-modified and do not contain a modifying acid or a modifying diol.

Examples of modifying acid components may include, but are not limited to, isophthalic acid, phthalic acid, 1,3-cyclohexanedicarboxylic acid, 1,4-cyclohexane dicarboxylic acid, 2,6-naphthaline dicarboxylic acid, succinic acid, glutaric acid, adipic acid, sebacic acid, suberic acid, 1,12-dodecanedioic acid, and the like. In practice, it is often preferable to use a functional acid derivative thereof such as the dimethyl, diethyl, or dipropyl ester of the dicarboxylic acid. The anhydrides or acid halides of these acids also may be employed where practical. Preferred is isophthalic acid.

Examples of modifying diol components may include, but are not limited to, neopentyl glycol, 1,4-cyclohexanedimethanol, 1,2-propanediol, 1,3-propanediol, 2-Methy-1,3-propanediol, 1,4-butanediol, 1,6-hexanediol, 1,2-cyclohexanediol, 1,4-cyclohexanediol, 1,2-cyclohexanedimethanol, 1,3-cyclohexanedimethanol, 2,2,4,4-tetramethyl 1,3-cyclobutane diol, Z,8-bis(hydroxymethyltricyclo-[5.2.1.0]-decane wherein Z represents 3, 4, or 5; 1,4-Bis(2-hydroxyethoxy)benzene, 4,4'-Bis(2-hydroxyethoxy)diphenylether [Bis-hydroxyethyl Bisphenol A], 4,4'-Bis(2-hydroxyethoxy)diphenylsulfide [Bis-hydroxyethyl Bisphenol S] and diols containing one or more oxygen atoms in the chain, e.g. diethylene glycol, triethylene glycol, dipropylene glycol, tripropylene glycol, and the like. In general, these diols contain 2 to 18, preferably 2 to 8 carbon atoms. Cycloalphatic diols can be employed in their cis or trans configuration or as mixtures of both forms.

When present, the polyester polymer or polycarbonate polymer combined with the polybutylene terephthalate can be added to the polymer composition in amounts generally greater than about 5% by weight, such as in amounts greater than about 10% by weight, such as in amounts greater than about 15% by weight, such as in amounts greater than about 20% by weight. The polyester polymer or polycarbonate polymer is generally present in an amount less than about 40% by weight, such as in an amount less than about 30% by weight, such as in an amount less than about 20% by weight, such as in an amount less than about 15% by weight.

Reinforcing Fibers

The polymer composition also contains reinforcing fibers in addition to the thermoplastic polymer matrix.

Reinforcing fibers of which use may advantageously be made are mineral fibers, such as glass fibers, polymer fibers, in particular organic high-modulus fibers, such as aramid fibers, or metal fibers, such as steel fibers, or carbon fibers or natural fibers, fibers from renewable resources.

These fibers may be in modified or unmodified form, e.g. provided with a sizing, or chemically treated, in order to improve adhesion to the plastic. Glass fibers are particularly preferred.

Glass fibers are provided with a sizing to protect the glassfiber, to smooth the fiber but also to improve the adhesion between the fiber and the matrix material. A sizing usually comprises silanes, film forming agents, lubricants, wetting agents, adhesive agents optionally antistatic agents and plasticizers, emulsifiers and optionally further additives.

Specific examples of silanes are aminosilanes, e.g. 3-trimethoxysilylpropylamine, N-(2-aminoethyl)-3-aminopropyltrimethoxy-silane, N-(3-trimethoxysilanylpropyl)ethane-1,2-diamine, 3-(2-aminoethyl-amino)propyltrimethoxysilane, N-[3-(trimethoxysilyl)propyl]-1,2-ethane-diamine.

Film forming agents are for example polyvinylacetates, polyesters and polyurethanes. Sizings based on polyurethanes may be used advantageously.

The reinforcing fibers may be compounded into the polymer matrix, for example in an extruder or kneader.

According to one embodiment, the molding composition of the present disclosure comprises at least one reinforcing fiber which is a mineral fiber, preferably a glass fiber, more preferably a coated or impregnated glass fiber. Glass fibers which are suitable for the molding composition of the present disclosure are commercially available, e.g. Johns Manville, ThermoFlow®Chopped Strand 753, OCV Chopped Strand 408 A, Nippon Electric Glass Co. (NEG) Chopped Strand T-651.

Fiber diameters can vary depending upon the particular fiber used and whether the fiber is in either a chopped or a continuous form. The fibers, for instance, can have a diameter of from about 5 μm to about 100 μm, such as from about 5 μm to about 50 μm, such as from about 5 μm to about 15 μm. The length of the fibers can vary depending upon the particular application. For instance, the fibers can have a length of greater than about 100 microns, such as greater than about 200 microns, such as greater than about 300 microns, such as greater than about 350 microns. The length of the fibers can generally be less than about 1,000 microns, such as less than about 800 microns, such as less than about 600 microns, such as less than about 500 microns. Once incorporated into the polymer composition and molded into an article, the fiber length can decrease. For instance, the average fiber length in the final product can be from about 100 microns to about 400 microns, such as from about 100 microns to about 300 microns.

In general, reinforcing fibers are present in the polymer composition in amounts sufficient to increase the tensile strength of the composition. The reinforcing fibers, for example, can be present in the polymer composition in an amount greater than about 5% by weight, such as in an amount greater than about 10% by weight, such as in an amount greater than about 15% by weight, such as in an amount greater than about 20% by weight, such as in an amount greater than about 25% by weight, such as in an amount greater than about 30% by weight. The reinforcing fibers are generally present in an amount less than about 55% by weight, such as in an amount less than about 50% by weight, such as in an amount less than about 45% by weight, such as in an amount less than about 40% by weight, such as in an amount less than about 35% by weight, such as in an amount less than about 30% by weight.

Tribological Modifier

According to the present disclosure, the polymer composition and the polymer article comprising the reinforced polyester polymer composition may comprise at least one tribological modifier.

In one embodiment, ultra-high molecular weight silicone (UHMW-Si) may be used to modify the polyester polymer. In general, the UHMW-Si can have an average molecular weight of greater than 100,000 g/mol, such as greater than about 200,000 g/mol, such as greater than about 300,000 g/mol, such as greater than about 500,000 g/mol and less than about 3,000,000 g/mol, such as less than about 2,000,000 g/mol, such as less than about 1,000,000 g/mol, such as less than about 500,000 g/mol, such as less than about 300,000 g/mol. Generally, the UHMW-Si can have a kinematic viscosity at 40° C. measured according to DIN 51562 of greater than 100,000 $mm^2s^{-1}$, such as greater than about 200,000 $mm^2s^{-1}$, such as greater than about 1,000,000 $mm^2s^{-1}$, such as greater than about 5,000,000 $mm^2s^{-1}$, such as greater than about 10,000,000 $mm^2s^{-1}$, such as greater than about 15,000,000 $mm^2s^{-1}$ and less than about 50,000,000 $mm^2s^{-1}$, such as less than about 25,000,000 $mm^2s^{-1}$, such as less than about 10,000,000 $mm^2s^{-1}$, such as less than about 1,000,000 $mm^2s^{-1}$, such as less than about 500,000 $mm^2s^{-1}$, such as less than about 200,000 $mm^2s^{-1}$.

The UHMW-Silicone may comprise a siloxane such as a polysiloxane or polyorganosiloxane. In one embodiment, the UHMW-Si may comprise a dialkylpolysiloxane such as a dimethylsiloxane, an alkylarylsiloxane such as a phenylmethylsiloxane, a polysilsesquioxane, or a diarylsiloxane such as a diphenylsiloxane, or a homopolymer thereof such as a polydimethylsiloxane or a polymethylphenylsiloxane, or a copolymer thereof with the above molecular weight and/or kinematic viscosity requirements. The polysiloxane or polyorganosiloxane may also be modified with a substituent such as an epoxy group, a hydroxyl group, a carboxyl group, an amino group or a substituted amino group, an ether group, or a meth(acryloyl) group in the end or main chain of the molecule. The UHMW-Si compounds may be used singly or in combination. Any of the above UHMW-Si compounds may be used with the above molecular weight and/or kinematic viscosity requirements.

The UHMW-Silicone may be added to the polymer composition as a masterbatch wherein the UHMW-Si is dispersed in a carrier polymer and the masterbatch is thereafter added to the composition. The masterbatch may comprise from about 10 wt. % to about 60 wt. %, such as from about 35 wt. % to about 55 wt. %, such as about 50 wt. % of an UHMW-Si.

The carrier polymer can vary depending upon the particular application and the desired result. The carrier polymer for the ultra-high molecular weight silicone may comprise any thermoplastic polymer compatible with polybutylene terephthalate. In one embodiment, for instance, the carrier polymer may comprise a polyester polymer. Using a polyester polymer, for instance, will assist in blending the ultra-high molecular weight silicone polymer with the polybutylene terephthalate polymer. The polyester carrier polymer, for instance, may comprise polybutylene terephthalate, polyethylene terephthalate, a copolyester, and/or a polyester elastomer. The polyester elastomer may comprise a copolyester such as a segmented thermoplastic copolyester. The polyester elastomer, for example, may comprise a multi-block copolymer. In an alternative embodiment, the carrier polymer may comprise a polycarbonate polymer.

In an alternative embodiment, instead of using a carrier polymer, the ultra-high molecular weight silicone polymer may be grafted onto particles that are then incorporated into the polymer composition. For instance, in one embodiment, the ultra-high molecular weight silicone polymer can be grafted on metal oxide particles such as silica particles. The ultra-high molecular weight silicone grafted silica can then be present in the composition in an amount greater than about 1% by weight, such as in an amount greater than about 2% by weight, such as in an amount greater than about 3% by weight, such as in an amount greater than about 4% by weight. The ultra-high molecular weight silicone grafted silica is generally present in the composition in an amount less than about 20% by weight, such as in an amount less than about 15% by weight, such as in an amount less than about 10% by weight, such as in an amount less than about 6% by weight.

The UHMW-Silicone may be present in the polymer composition in an amount of at greater than about 0.005 wt. %, such as at greater than about 0.1 wt. %, such as at greater than about 0.5 wt. %, such as at greater than about 0.75 wt. %, such as at greater than about 1 wt. %, such as at greater than about 2 wt. %, such as at greater than about 2.5 wt. % and generally less than about 10 wt. %, such as less than about 6 wt. %, such as less than about 5 wt. %, such as less than about 4 wt. %, such as less than about 3.5 wt. %, such as less than about 3 wt. %, wherein the weight is based on the total weight of the polymer composition.

In an alternative embodiment, the at least one tribological additive may comprise a fluoropolymer, such as polytetrafluoroethylene powder. The fluoropolymer may be combined with the ultra-high molecular weight silicone in one application. The polytetrafluoroethylene particles, for instance, can have an average particle size of less than about 15 microns, such as less than about 12 microns, such as less than about 10 microns, such as less than about 8 microns.

The average particle size of the polytetrafluoroethylene particles is generally greater than about 0.5 microns, such as greater than about 1 micron, such as greater than about 2 microns, such as greater than about 3 microns, such as greater than about 4 microns, such as greater than about 5 microns. Average particle size can be measured according to ISO Test 13321.

In one embodiment, the polytetrafluoroethylene particles can have a relatively low molecular weight. The polytetrafluoroethylene polymer may have a density of from about 300 g/l to about 450 g/l, such as from about 325 g/l to about 375 g/l when tested according to ASTM Test D4895. The polytetrafluoroethylene particles can have a specific surface area of from about 5 $m^2$/g to about 15 $m^2$/g, such as from about 8 $m^2$/g to about 12 $m^2$/g when tested according to Test DIN66132. The melt flow rate of the polytetrafluoroethylene polymer can be less than about 3 g/10 min, such as less than about 2 g/10 min when tested according to ISO Test 1133 when carried out at 372° C. with a load of 10 kg.

The polytetrafluoroethylene particles can be present in the polymer composition in an amount greater than about 1% by weight, such as in an amount greater than about 2% by weight, such as in an amount greater than about 3% by weight, such as in an amount greater than about 4% by weight. The polytetrafluoroethylene polymer is generally present in the polymer composition in an amount less than about 20% by weight, such as in an amount less than about 15% by weight, such as in an amount less than about 10% by weight, such as in an amount less than about 8% by weight.

According to the present disclosure, the tribological additives improve the tribological properties of the polymer compositions and polymer articles produced therefrom without the need for an external lubricant, such as water-based external lubricants, when utilized in tribological applications. An external lubricant may be a lubricant that is applied to a polymer article. In one embodiment, an external lubricant may not be associated with the polymer composition or polymer article such that the external lubricant is not present on a surface of the polymer composition or polymer article. In another embodiment, an external lubricant may be utilized with the polymer composition and polymer article of the present disclosure.

In addition to an ultra-high molecular weight silicone and/or a polytetrafluoroethylene polymer, the polymer composition may contain other tribological modifiers. Other tribological modifiers that may be present include, for instance, boron nitride, ultra-high molecular weight polyethylene particles, stearyl stearate particles, waxes, and the like. The other tribological modifiers can generally be present in an amount from about 0.5% to about 5% by weight, such as in an amount from about 1% to about 3% by weight.

Other Additives

The polymer composition of the present disclosure can contain various other additives. For example, the composition may further include a nucleating agent, present in a concentration of between about 0.1 and 2% by weight, preferably between about 0.001% and 0.5% based on the total weight of the composition. The nucleating agent can be selected from the group consisting of alkali metal salts having anions which are oxides of the elements from Group IV of the Periodic Table; barium sulfate; and talc.

The polymer composition may also contain at least one stabilizer. The stabilizer may comprise an antioxidant, a light stabilizer such as an ultraviolet light stabilizer, a thermal stabilizer, and the like.

Sterically hindered phenolic antioxidant(s) may be employed in the composition. Examples of such phenolic antioxidants include, for instance, calcium bis(ethyl 3,5-di-tert-butyl-4-hydroxybenzylphosphonate) (Irganox® 1425); terephthalic acid, 1,4-dithio-,S,S-bis(4-tert-butyl-3-hydroxy-2,6-dimethylbenzyl) ester (Cyanox®1729); triethylene glycol bis(3-tert-butyl-4-hydroxy-5-methylhydrocinnamate); hexamethylene bis(3,5-di-tert-butyl-4-hydroxyhydrocinnamate (Irganox® 259); 1,2-bis(3,5,di-tert-butyl-4-hydroxyhydrocinnamoyl)hydrazide (Irganox® 1024); 4,4'-di-tert-octyldiphenamine (Naugalube® 438R); phosphonic acid, (3,5-di-tert-butyl-4-hydroxybenzyl)-,dioctadecyl ester (Irganox® 1093); 1,3,5-trimethyl-2,4,6-tris(3',5'-di-tert-butyl-4' hydroxybenzyl)benzene (Irganox®1330); 2,4-bis(octylthio)-6-(4-hydroxy-3,5-di-tert-butylanilino)-1,3,5-trazine (Irganox® 565); isooctyl 3-(3,5-di-tert-butyl-4-hydroxyphenyl)propionate (Irganox® 1135); octadecyl 3-(3,5-di-tert-butyl-4-hydroxyphenyl)propionate (Irganox® 1076); 3,7-bis(1,1,3,3-tetramethylbutyl)-10H-phenothiazine (Irganox® LO 3); 2,2'-methylenebis(4-methyl-6-tert-butylphenol)monoacrylate (Irganox® 3052); 2-tert-butyl-6-[1-(3-tert-butyl-2-hydroxy-5-methylphenyl)ethyl]-4-methylphe nyl acrylate (Sumilizer® TM 4039); 2-[1-(2-hydroxy-3,5-di-tert-pentylphenyl)ethyl]-4,6-di-tert-pentylphenyl acrylate (Sumilizer® GS); 1,3-dihydro-2H-Benzimidazole (Sumilizer® MB); 2-methyl-4,6-bis[(octylthio)methyl]phenol (Irganox® 1520); N,N'-trimethylenebis-[3-(3,5-di-tert-butyl-4-hydroxyphenyl)propionamide (Irganox® 1019); 4-n-octadecyloxy-2,6-diphenylphenol (Irganox® 1063); 2,2'-ethylidenebis[4,6-di-tert-butylphenol](Irganox® 129); N N'-hexamethylenebis(3,5-di-tert-butyl-4-hydroxyhydrocinnamamide) (Irganox® 1098); diethyl (3,5-di-tert-butyl-4-hydroxybenxyl)phosphonate (Irganox® 1222); 4,4'-di-tert-octyldiphenylamine (Irganox® 5057); N-phenyl-1-naptha lenamine (Irganox® L 05); tris[2-tert-butyl-4-(3-ter-butyl-4-hydroxy-6-methylphenylthio)-5-methyl phenyl]phosphite (Hostanox® OSP 1); zinc dinonyidithiocarbamate (Hostanox® VP-ZNCS 1); 3,9-bis[1,1-diimethyl-2-[(3-tert-butyl-4-hydroxy-5-methylphenyl)propionyloxy]ethyl]-2,4, 8,10-tetraoxaspiro[5.5]undecane (SumilizerS AG80); pentaerythrityl tetrakis[3-(3,5-di-tert-butyl-4-hydroxyphenyl)propionate] (Irganox® 1010); ethylene-bis(oxyethylene)bis[3-(5-tert-butyl-4-hydroxy-m-tolyl)-propionate (Irganox® 245); 3,5-di-tert-butyl-4-hydroxytoluene (Lowinox BHT, Chemtura) and so forth.

Some examples of suitable sterically hindered phenolic antioxidants for use in the present composition are triazine antioxidants having the following general formula:

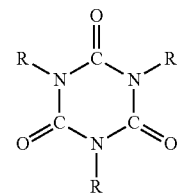

wherein, each R is independently a phenolic group, which may be attached to the triazine ring via a $C_1$ to $C_5$ alkyl or an ester substituent. Preferably, each R is one of the following formula (I)-(III):

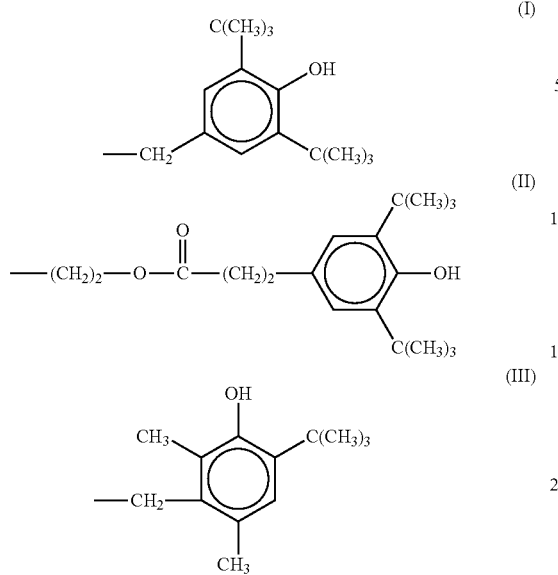

Commercially available examples of such triazine-based antioxidants may be obtained from American Cyanamid under the designation Cyanox® 1790 (wherein each R group is represented by the Formula III) and from Ciba Specialty Chemicals under the designations Irganox® 3114 (wherein each R group is represented by the Formula I) and Irganox® 3125 (wherein each R group is represented by the Formula II).

Sterically hindered phenolic antioxidants may constitute from about 0.01 wt. % to about 3 wt. %, in some embodiments from about 0.05 wt. % to about 1 wt. %, and in some embodiments, from about 0.05 wt. % to about 0.1 wt. % of the entire stabilized polymer composition. In one embodiment, for instance, the antioxidant comprises pentaerythrityl tetrakis[3-(3,5-di-tert-butyl-4-hydroxyphenyl)propionate.

embodiments from about 1000 to about 20,000, in some embodiments from about 1500 to about 15,000, and in some embodiments, from about 2000 to about 5000. Such compounds typically contain at least one 2,2,6,6-tetraalkylpiperidinyl group (e.g., 1 to 4) per polymer repeating unit.

Without intending to be limited by theory, it is believed that high molecular weight hindered amines are relatively thermostable and thus able to inhibit light degradation even after being subjected to extrusion conditions. One particularly suitable high molecular weight hindered amine has the following general structure:

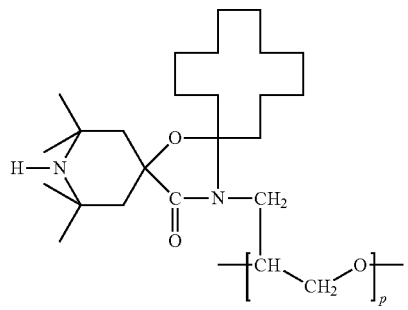

wherein, p is 4 to 30, in some embodiments 4 to 20, and in some embodiments 4 to 10. This oligomeric compound is commercially available from Clariant under the designation Hostavin® N30 and has a number average molecular weight of 1200.

Another suitable high molecular weight hindered amine has the following structure:

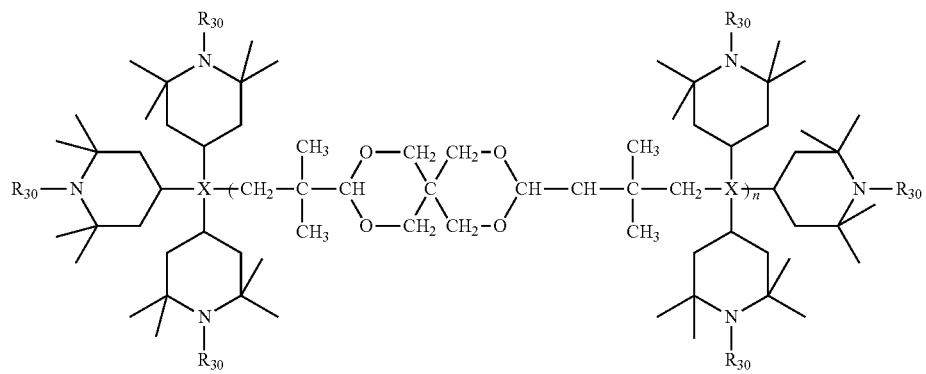

Hindered amine light stabilizers ("HALS") may be employed in the composition to inhibit degradation of the polyester composition and thus extend its durability. Suitable HALS compounds may be derived from a substituted piperidine, such as alkyl-substituted piperidyl, piperidinyl, piperazinone, alkoxypiperidinyl compounds, and so forth. For example, the hindered amine may be derived from a 2,2,6,6-tetraalkylpiperidinyl. Regardless of the compound from which it is derived, the hindered amine is typically an oligomeric or polymeric compound having a number average molecular weight of about 1,000 or more, in some wherein, n is from 1 to 4 and $R_{30}$ is independently hydrogen or $CH_3$. Such oligomeric compounds are commercially available from Adeka Palmarole SAS (joint venture between Adeka Corp. and Palmarole Group) under the designation ADK STAB® LA-63 ($R_{30}$ is $CH_3$) and ADK STAB® LA-68 ($R_{30}$ is hydrogen).

Other examples of suitable high molecular weight hindered amines include, for instance, an oligomer of N-(2-hydroxyethyl)-2,2,6,6-tetramethyl-4-piperidinol and succinic acid (Tinuvin® 622 from Ciba Specialty Chemicals, MW=4000): oligomer of cyanuric acid and N,N-di(2,2,6,6- tetramethyl-4-piperdyl)-hexamethylene diamine; poly((6-morpholine-S-triazine-2,4-diyl)(2,2,6,6-tetramethyl-4-piperdinyl)-iminohexamethylene-(2,2,6,6-tetramethyl-4-piperidinyl)-imino) (Cyasorb® UV 3346 from Cytec, MW=1600); polymethylpropyl-3-oxy-[4(2,2,6,6-tetramethyl)-piperidinylysiloxane (Uvasil® 299 from Great Lakes Chemical, MW=1100 to 2500); copolymer of α-methylstyrene-N-(2,2,6,6-tetramethyl-4-piperidinyl)maleimide and N-stearyl maleimide; 2,4,8,10-tetraoxaspiro[5.5]undecane-3,9-diethanol tetramethyl-polymer with 1,2,3,4-butanetetracarboxylic acid; and so forth. Still other suitable high molecular weight hindered amines are described in U.S. Pat. No. 5,679,733 to Malik, et al. and U.S. Pat. No. 6,414,155 to Sassi, et al., which are incorporated herein in their entirety by reference thereto for all purposes.

In addition to the high molecular hindered amines, low molecular weight hindered amines may also be employed in the composition. Such hindered amines are generally monomeric in nature and have a molecular weight of about 1000 or less, in some embodiments from about 155 to about 800, and in some embodiments, from about 300 to about 800.

Specific examples of such low molecular weight hindered amines may include, for instance, bis-(2,2,6,6-tetramethyl-4-piperidyl) sebacate (Tinuvin® 770 from Ciba Specialty Chemicals, MW=481); bis-(1,2,2,6,6-pentamethyl-4-piperdinyl)-(3,5-ditert.butyl-4-hydroxybenzyl)butyl-propane dioate; bis-(1,2,2,6,6-pentamethyl-4-piperidinyl)sebacate; 8-acetyl-3-dodecyl-7,7,9,9-tetramethyl-1,3,8-triazaspiro-(4,5)-decane-2,4-dione, butanedioic acid-bis-(2,2,6,6-tetramethyl-4-piperidinyl) ester; tetrakis-(2,2,6,6-tetramethyl-4-piperidyl)-1,2,3,4-butane tetracarboxylate; 7-oxa-3,20-diazadispiro(5.1.11.2) heneicosan-20-propanoic acid, 2,2,4,4-tetramethyl-21-oxo, dodecyl ester; N-(2,2,6,6-tetramethyl-4-piperidinyl)-N'-amino-oxamide; o-t-amyl-o-(1,2,2,6,6-pentamethyl-4-piperidinyl)-monoperoxi-carbonate; β-alanine, N-(2,2,6,6-tetramethyl-4-piperdinyl), dodecylester; ethanediamide, N-(1-acetyl-2,2,6,6-tetramethylpiperdinyl)-N'-dodecyl; 3-dodecyl-1-(2,2,6,6-tetramethyl-4-piperidinyl)-pyrrolidin-2,5-dione; 3-dodecyl-1-(1,2,2,6,6-pentamethyl-4-piperidinyl)-pyrrolidin-2,5-dione; 3-dodecyl-1-(1-acetyl,2,2,6,6-tetramethyl-4-piperidinyl)-pyrrolidin-2,5-dione, (Sanduvar® 3058 from Clariant, MW=448.7); 4-benzoyloxy-2,2,6,6-tetramethylpiperidine; 1-[2-(3,5-di-tert-butyl-4-hydroxyphenylpropionyloxy)ethyl]-4-(3,5-di-tert-butyl-4-hydroxyphenyl propionyloxy)-2,2,6,6-tetramethyl-piperdine; 2-methyl-2-(2",2",6",6"-tetramethyl-4"-piperidinylamino)-N-(2',2',6',6'-tetra-methyl-4'-piperdinyl)propionylamide; 1,2-bis-(3,3,5,5-tetramethyl-2-oxo-piperazinyl)ethane; 4-oleoyloxy-2,2,6,6-tetramethylpiperidine; and combinations thereof. Other suitable low molecular weight hindered amines are described in U.S. Pat. No. 5,679,733 to Malik, et al.

The hindered amines may be employed singularly or in combination in any amount to achieve the desired properties, but typically constitute from about 0.01 wt. % to about 4 wt. % of the polymer composition.

UV absorbers, such as benzotriazoles or benzopheones, may be employed in the composition to absorb ultraviolet light energy. Suitable benzotriazoles may include, for instance, 2-(2-hydroxyphenyl)benzotriazoles, such as 2-(2-hydroxy-5-methylphenyl)benzotriazole: 2-(2-hydroxy-5-tert-octylphenyl)benzotriazole (Cyasorb® UV 5411 from Cytec); 2-(2-hydroxy-3,5-di-tert-butylphenyl)-5-chlorobenzo-triazole; 2-(2-hydroxy-3-tert-butyl-5-methylphenyl)-5-chlorobenzotriazole; 2-(2-hydroxy-3,5-dicumylphenyl)benzotriazole; 2,2'-methylenebis(4-tert-octyl-6-benzo-triazolylphenol); polyethylene glycol ester of 2-(2-hydroxy-3-tert-butyl-5-carboxyphenyl)benzotriazole; 2-[2-hydroxy-3-(2-acryloyloxyethyl)-5-methylphenyl]-benzotriazole; 2-[2-hydroxy-3-(2-methacryloyloxyethyl)-5-tert-butylphenyl]benzotriazole; 2-[2-hydroxy-3-(2-methacryloyloxyethyl)-5-tert-octylphenyl]benzotriazole; 2-[2-hydroxy-3-(2-methacryloyloxyethyl)-5-tert-butylphenyl]-5-chlorobenzotriazole; 2-[2-hydroxy-5-(2-methacryloyloxyethyl)phenyl]benzotriazole; 2-[2-hydroxy-3-tert-butyl-5-(2-methacryloyloxyethyl)phenyl]benzotriazole; 2-[2-hydroxy-3-tert-amyl-5-(2-methacryloyloxyethyl)phenyl]benzotriazole; 2-[2-hydroxy-3-tert-butyl-5-(3-methacryloyloxypropyl)phenyl]-5-chlorobenzotriazole; 2-[2-hydroxy-4-(2-methacryloyloxymethyl)phenyl]benzotriazole; 2-[2-hydroxy-4-(3-methacryloyloxy-2-hydroxypropyl)phenyl]benzotriazole; 2-[2-hydroxy-4-(3-methacryloyloxypropyl)phenyl]benzotriazole; and combinations thereof.

Exemplary benzophenone light stabilizers may likewise include 2-hydroxy-4-dodecyloxybenzophenone: 2,4-dihydroxybenzophenone; 2-(4-benzoyl-3-hydroxyphenoxy) ethyl acrylate (Cyasorb® UV 209 from Cytec); 2-hydroxy-4-n-octyloxy)benzophenone (Cyasorb® 531 from Cytec); 2,2'-dihydroxy-4-(octyloxy)benzophenone (Cyasorb® UV 314 from Cytec); hexadecyl-3,5-bis-tert-butyl-4-hydroxybenzoate (Cyasorb® UV 2908 from Cytec); 2,2'-thiobis(4-tert-octylphenolato)-n-butylamine nickel(II) (Cyasorb® UV 1084 from Cytec); 3,5-di-tert-butyl-4-hydroxybenzoic acid, (2,4-di-tert-butylphenyl)ester (Cyasorb® 712 from Cytec); 4,4'-dimethoxy-2,2'-dihydroxybenzophenone (Cyasorb® UV 12 from Cytec); and combinations thereof.

When employed, UV absorbers may constitute from about 0.01 wt. % to about 4 wt. % of the entire polymer composition.

In one embodiment, the polymer composition may contain a blend of stabilizers that produce ultraviolet resistance and color stability. The combination of stabilizers may allow for products to be produced that have bright and fluorescent colors. In addition, bright colored products can be produced without experiencing significant color fading over time. In one embodiment, for instance, the polymer composition may contain a combination of a benzotriazole light stabilizer and a hindered amine light stabilizer, such as an oligomeric hindered amine.

If desired, fatty acid esters may be present as lubricants. Fatty acid esters may be obtained by oxidative bleaching of a crude natural wax and subsequent esterification of the fatty acids with an alcohol. The alcohol typically has 1 to 4 hydroxyl groups and 2 to 20 carbon atoms. When the alcohol is multifunctional (e.g., 2 to 4 hydroxyl groups), a carbon atom number of 2 to 8 is particularly desired. Particularly suitable multifunctional alcohols may include dihydric alcohol (e.g., ethylene glycol, propylene glycol, butylene glycol, 1,3-propanediol, 1,4-butanediol, 1,6-hexanediol and 1,4-cyclohexanediol), trihydric alcohol (e.g., glycerol and trimethylolpropane), tetrahydric alcohols (e.g., pentaerythritol and erythritol), and so forth. Aromatic alcohols may also be suitable, such as o-, m- and p-tolylcarbinol, chlorobenzyl alcohol, bromobenzyl alcohol, 2,4-dimethylbenzyl alcohol, 3,5-dimethylbenzyl alcohol, 2,3,5-cumobenzyl alcohol, 3,4, 5-trimethylbenzyl alcohol, p-cuminyl alcohol, 1,2-phthalyl alcohol, 1,3-bis(hydroxymethyl)benzene, 1,4-bis(hydroxymethyl)benzene, pseudocumenyl glycol, mesitylene glycol and mesitylene glycerol. Particularly suitable fatty acid esters for use in the present invention are derived from montanic waxes. Licowax® OP (Clariant), for instance, contains montanic acids partially esterified with butylene glycol and montanic acids partially saponified with calcium hydroxide. Thus, Licowax® OP contains a mixture of montanic acid esters and calcium montanate. Other montanic acid esters that may be employed include Licowax® E, Licowax® OP, and Licolub® WE 4 (all from Clariant), for instance, are montanic esters obtained as secondary products from the oxidative refining of raw montan wax. Licowax® E and Licolub® WE 4 contain montanic acids esterified with ethylene glycol or glycerine.

Other known waxes may also be employed in a lubricant. Amide waxes, for instance, may be employed that are formed by reaction of a fatty acid with a monoamine or diamine (e.g., ethylenediamine) having 2 to 18, especially 2 to 8, carbon atoms. For example, ethylenebisamide wax, which is formed by the amidization reaction of ethylene diamine and a fatty acid, may be employed. The fatty acid may be in the range from $C_{12}$ to $C_{30}$, such as from stearic acid (Cia fatty acid) to form ethylenebisstearamide wax. Ethylenebisstearamide wax is commercially available from Lonza, Inc. under the designation Acrawax® C, which has a discrete melt temperature of 142° C. Other ethylenebisamides include the bisamides formed from lauric acid, palmitic acid, oleic acid, linoleic acid, linolenic acid, oleostearic acid, myristic acid and undecalinic acid. Still other suitable amide waxes are N-(2-hydroxyethyl)12-hydroxystearamide and N,N'-(ethylene bis)12-hydroxystearamide.

In addition to the above components, the polymer composition may include various other ingredients. Colorants that may be used include any desired inorganic pigments, such as titanium dioxide, ultramarine blue, cobalt blue, and other organic pigments and dyes, such as phthalocyanines, anthraquinones, and the like. Other colorants include carbon black or various other polymer-soluble dyes. The colorants can generally be present in the composition in an amount up to about 2 percent by weight.

Polymer Articles

The compositions of the present disclosure can be compounded and formed into a polymer article using any technique known in the art. For instance, the respective composition can be intensively mixed to form a substantially homogeneous blend. The blend can be melt kneaded at an elevated temperature, such as a temperature that is higher than the melting point of the polymer utilized in the polymer composition but lower than the degradation temperature. Alternatively, the respective composition can be melted and mixed together in a conventional single or twin screw extruder. Preferably, the melt mixing is carried out at a temperature ranging from 150 to 300° C., such as from 200 to 280° C., such as from 220 to 270° C. or 240 to 260° C. However, such processing should be conducted for each respective composition at a desired temperature to minimize any polymer degradation.

After extrusion, the compositions may be formed into pellets. The pellets can be molded into polymer articles by techniques known in the art such as injection molding, thermoforming, blow molding, rotational molding and the like. According to the present disclosure, the polymer articles demonstrate excellent tribological behavior and mechanical properties. Consequently, the polymer articles can be used for several applications where low wear and excellent gliding properties are desired.

Polymer articles include any moving articles or moldings that are in contact with another surface and may require high tribological requirements. For instance, polymer articles include articles for the automotive industry, especially housings, latches such as rotary latches, window winding systems, wiper systems, pulleys, sun roof systems, seat adjustments, levers, bushes, gears, gear boxes, claws, pivot housings, wiper arms, brackets or seat rail bearings, zippers, switches, cams, rollers or rolling guides, sliding elements or glides such as sliding plates, conveyor belt parts such as chain elements and links, castors, fasteners, levers, conveyor system wear strips and guard rails, medical equipment such as medical inhalers and injectors. An almost limitless variety of polymer articles may be formed from the polymer compositions of the present disclosure.

In one embodiment, the composition of the present disclosure is used to produce a first sliding member and a second sliding member. The first and second sliding members can both be made from a composition in accordance with the present disclosure. In particular, the first sliding member and the second sliding member can be made from a composition comprising a reinforced polyester polymer in combination with an ultrahigh molecular weight silicone and optionally a fluoropolymer. The relative amounts of the components can be the same or can be different in each composition.

The first sliding member and the second sliding member can be contained in an apparatus and placed in operative association with each other such that the sliding members move relative to each other. For instance, in one embodiment, the first sliding member may be stationary while the second sliding member moves across the first sliding member. Alternatively, both sliding members may move while contacting each other.

In one embodiment, the sliding members of the present disclosure can be used to produce a medical product. For instance, referring to FIG. 1, an inhaler 20 is shown. The inhaler 20 includes a housing 22 attached to a mouthpiece 24. In operative association with the housing 22 is a plunger 26 for receiving a canister containing a composition to be inhaled. The composition may comprise a spray or a powder. The inhaler 20 can include a first sliding member in operative association with a second sliding member. For instance, in certain embodiments, the housing 22 may comprise the first sliding member while the plunger 26 may comprise the second sliding member. Alternatively, the first sliding member may comprise the housing 22 and the second sliding member may comprise the mouthpiece 24. In still another embodiment, an internal sliding member may be contained within the housing 22 that slides relative to the housing.

During use, the inhaler 20 administers metered doses of a medication, such as an asthma medication to a patient. The asthma medication may be suspended or dissolved in a propellant or may be contained in a powder. When a patient actuates the inhaler to breathe in the medication, a valve opens allowing the medication to exit the mouthpiece.

Figure 2:
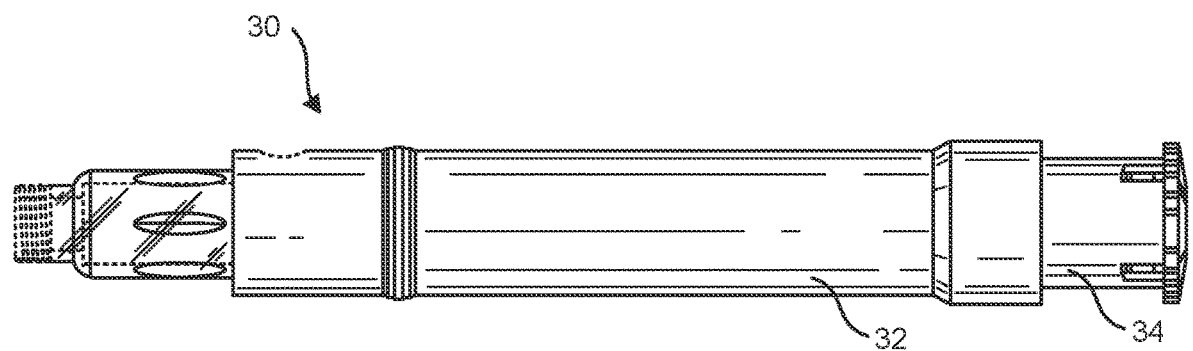
FIG. 2 is a side view of a medical injector that may be made in accordance with the present disclosure.

In another embodiment of the present disclosure, the first sliding member and the second sliding member are contained in a medical injector 30 as shown in FIG. 2. The medical injector 30 includes a housing 32 in operative association with a plunger 34. The housing 32 or first sliding member may slide relative to the plunger 34 or second sliding member. The medical injector 30 may be spring loaded. The medical injector 30 is for injecting a drug into a patient, typically into the thigh or the buttocks. The medical injector can be needleless or may contain a needle. When containing a needle, the needle tip is typically shielded within the housing prior to injection. Needleless injectors, on the other hand, can contain a cylinder of pressurized gas that propels a medication through the skin without the use of a needle.

Properties

The polyester polymer composition and polymer articles produced therefrom according to the present disclosure have improved tribological properties. According to the present disclosure, the tribological properties are generally measured by the coefficient of friction.

In general, static friction is the friction between two or more surfaces that are not moving relative to each other (i.e., both objects are stationary). In general, dynamic friction occurs when two objects are moving relative to each other (i.e., at least one object is in motion or repeated back and forth motion). In addition, stick-slip is generally known as a phenomenon caused by continuous alternating between static and dynamic friction.

According to the present disclosure, the composition and polymer article may exhibit a dynamic coefficient of friction against another surface, as determined according to VDA 230-206, of less than about 0.08, such as less than about 0.07, such as less than about 0.06, such as less than about 0.05.

In one embodiment, the above dynamic coefficient of friction values and effect of sliding speed on the dynamic coefficient of friction are exhibited between the composition or polymer article and various counter-materials. For instance, the above values may be exhibited between the composition or polymer article and an identical composition or article.

The counter-material may also comprise a polycarbonate polymer composition containing 20% by weight glass fiber and 15% by weight polytetrafluoroethylene particles. In another embodiment, the counter-material comprises a polybutylene terephthalate composition containing 20% by weight glass fiber and 15% by weight polytetrafluoroethylene particles.

While the polymer composition and polymer articles produced therefrom of the present disclosure provide improved tribological properties, the compositions and articles may also exhibit improved mechanical properties. For instance, the tensile modulus, determined according to ISO Test No. 527, of the composition or polymer article may be greater than about 7000 MPa, such as greater than about 7200 MPa, such as greater than about 7500 MPa, and generally less than about 15,000 MPa, such as less than about 10,000 MPa.

The break stress of the composition can generally be greater than about 100 MPa, such as greater than about 110 MPa, such as greater than about 115 MPa, such as greater than about 120 MPa and generally less than about 180 MPa. The break strain can generally be greater than about 2.0%, such as greater than about 2.5%, and generally less than about 4%. The composition can exhibit a Charpy notched impact strength when tested at 23° C. of greater than about 6 kJ/m$^2$, such as greater than about 8 kJ/m$^2$, such as greater than about 9 kJ/m$^2$ and generally less than about 20 kJ/m$^2$, such as less than about 15 kJ/m$^2$.

The present disclosure may be better understood with reference to the following examples.

EXAMPLE

The following example is given below by way of illustration and not by way of limitation. The following experiments were conducted in order to show some of the benefits and advantages of the present invention.

Various polymer compositions containing glass fibers and a tribological modifier were formulated and tested for friction characteristics and physical properties. Each of the compositions contained a polybutylene terephthalate polymer and glass fibers in an amount of 22% by weight. An ultra-high molecular weight silicone was then added to the composition with different carriers. In one embodiment, for instance, the carrier was silica particles. In other embodiments, however, the carrier was a polycarbonate polymer or a thermoplastic polyester elastomer. Some of the compositions also contained 5% by weight polytetrafluoroethylene particles. One formulation only contained polytetrafluoroethylene particles as the tribological modifier.

The components of each respective composition were mixed together and compounded using a ZSK 25MC (Werner & Pfleiderer, Germany) twin screw extruder. The screw configuration with kneading elements was chosen so that effective thorough mixing of the components took place. The compositions were extruded and pelletized. The pellets were dried for 8 hours at 120° C. and then injection molded.

The compositions/molds were tested for a variety of tribological and physical properties.

In this example, the tribological properties were determined for various compositions.

Stick-slip tests were conducted to determine the dynamic coefficient of friction. Stick-slip tests were conducted according to VDA 230-206. A ball-on-plate configuration was utilized with a load of 30 N, a sliding speed of 8 mm/s, and a test duration of 1000 cycles.

The compositions formulated according to the present disclosure were formed into plates for the dynamic coefficient of friction test. In a first set of experiments, the compositions were tested against a ball made from polycarbonate polymer containing 20% by weight glass fiber and 15% by weight polytetrafluoroethylene particles. The following results were obtained:

TABLE 1

| No. | Triboadditives in PBT with 22% GF | Dynamic CoF | Wear track width (mm) |
|---|---|---|---|
| 1 | 5% PTFE | 0.094 | 0.44 |
| 2 | 5% PTFE + 4.3% UHMW-Si grafted Silica | 0.07 | 0.45 |
| 3 | 5% PTFE + 3% UHMW-Si (50% blend in PC) | 0.043 | 0.66 |
| 4 | 5% PTFE + 3% UHMW-Si (50% blend in thermoplastic polyester elastomer) | 0.044 | 0.53 |
| 5 | 3% UHMW-Si (50% blend in thermoplastic polyester elastomer) | 0.039 | 0.57 |

In a second set of experiments, the ball was made from a polymer composition containing polybutylene terephthalate polymer combined with 20% by weight glass fiber and 15% by weight polytetrafluoroethylene particles. The following results were obtained:

TABLE 2

| No. | Triboadditives in PBT with 22% GF | Dynamic CoF | Wear track width (mm) |
|---|---|---|---|
| 1 | 5% PTFE | 0.093 | 0.33 |
| 2 | 5% PTFE + 4.3% UHMW-Si grafted Silica | 0.068 | 0.12 |
| 3 | 5% PTFE + 3% UHMW-Si (50% blend in PC) | 0.043 | 0.2 |
| 4 | 5% PTFE + 3% UHMW-Si (50% blend in thermoplastic polyester elastomer) | 0.041 | 0.15 |
| 5 | 3% UHMW-Si (50% blend in thermoplastic polyester elastomer) | 0.044 | 0.19 |

In a third set of experiments, the ball was made from the identical polymer composition. The following results were obtained:

TABLE 3

| No. | Triboadditives in PBT with 22% GF | Dynamic CoF | Wear track width (mm) |
|---|---|---|---|
| 1 | 5% PTFE | 0.091 | 0.34 |
| 2 | 5% PTFE + 4.3% UHMW-Si grafted Silica | 0.07 | 0.18 |
| 3 | 5% PTFE + 3% UHMW-Si (50% blend in PC) | 0.042 | 0.23 |
| 4 | 5% PTFE + 3% UHMW-Si (50% blend in thermoplastic polyester elastomer) | 0.043 | 0.19 |
| 5 | 3% UHMW-Si (50% blend in thermoplastic polyester elastomer) | 0.045 | 0.24 |

The compositions were also tested for physical properties. Tensile properties were tested according to ISO Test 527: 2012. Notched Charpy impact strength was tested according to ISO Test 179-1:2010. The test was run using a Type A notch (0.25 mm base radius) and Type 1 specimen size (length of 80 mm, width of 10 mm, and thickness of 4 mm). The test was conducted at a temperature of 23° C. The following results were obtained:

TABLE 4

| Property | Triboadditives in PBT with 22% GF | | | | |
|---|---|---|---|---|---|
| | 5% PTFE | 5% PTFE + 4.3% UHMW-Si grafted Silica | 5% PTFE + 3% UHMW-Si (50% blend in PC) | 5% PTFE + 3% UHMW-Si (50% blend in thermoplastic polyester elastomer) | 3% UHMW-Si (50% blend in thermoplastic polyester elastomer) |
| Tensile modulus (MPa) | 8280 | 7705 | 7810 | 7780 | 7750 |
| Break stress (MPa) | 136 | 115 | 122 | 120 | 121 |
| Break strain (%) | 2.9 | 2.8 | 2.9 | 2.7 | 2.6 |
| Charpy notched @ 23° C. (kJ/m$^2$) | 9.3 | 9.8 | 10 | 10.5 | 10.1 |

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A polymer composition that can be compounded or extruded into a polymer article comprising:
    a polyester polymer, the polyester polymer comprising a polybutylene terephthalate polymer alone or in combination with a polyethylene terephthalate polymer, the polybutylene terephthalate polymer being present in the polymer composition in an amount greater than 60% by weight;
    optionally reinforcing fibers present in the polymer composition in an amount from about 5% to about 35% by weight; and
    a masterbatch comprising a first tribological modifier dispersed in a carrier polymer, the first tribological modifier comprising an ultra-high molecular weight silicone having a kinematic viscosity of greater than 100,000 mm$^2$s$^{-1}$, the ultra-high molecular weight silicone being present in the polymer composition in an amount from about 0.5% by weight to about 6% by weight, the ultra-high molecular weight silicone being present in the masterbatch in an amount from about 35% by weight to about 60% by weight, and wherein the carrier polymer comprises a polyester elastomer.

2. The polymer composition that can be compounded or extruded into a polymer article as defined in claim 1, wherein the ultra-high molecular weight silicone is a polydimethylsiloxane.

3. The polymer composition that can be compounded or extruded into a polymer article as defined in claim 1, wherein the composition contains a second tribological modifier.

4. The polymer composition that can be compounded or extruded into a polymer article as defined in claim 3, wherein the polybutylene terephthalate polymer is present in the composition in an amount from about 70% to about 90% by weight, the reinforcing fibers comprising glass fibers and being present in the polymer composition in an amount from about 5% to about 30% by weight, and the ultra-high molecular weight silicone dispersed within the carrier polymer being present in the composition in an amount from about 0.5% to about 5% by weight.

5. The polymer composition that can be compounded or extruded into a polymer article as defined in claim 1, wherein the composition is isocyanate free.

6. The polymer composition that can be compounded or extruded into a polymer article as defined in claim 1, wherein the polymer composition exhibits a dynamic coefficient of friction according to VDA 230-206 of less than 0.08 when tested against polycarbonate containing 15% by weight polytetrafluoroethylene and 20% by weight glass fiber, when tested against polybutylene terephthalate containing 15% by weight polytetrafluoroethylene and 20% by weight glass fiber, or when tested against itself at a speed of 8 mm/s, at a load of 30 N and after 1,000 cycles.

7. The polymer composition that can be compounded or extruded into a polymer article as defined in claim 1, wherein the polymer composition exhibits a dynamic coefficient of friction according to VDA 230-206 of less than 0.07 when tested against polycarbonate containing 15% by weight polytetrafluoroethylene and 20% by weight glass fiber, when tested against polybutylene terephthalate containing 15% by weight polytetrafluoroethylene and 20% by weight glass fiber, or when tested against itself at a speed of 8 mm/s, at a load of 30 N and after 1,000 cycles.

8. The polymer composition that can be compounded or extruded into a polymer article as defined in claim 1, wherein the polymer composition exhibits a dynamic coefficient of friction according to VDA 230-206 of less than 0.05 when tested against polycarbonate containing 15% by weight polytetrafluoroethylene and 20% by weight glass fiber, when tested against polybutylene terephthalate containing 15% by weight polytetrafluoroethylene and 20% by weight glass fiber, or when tested against itself at a speed of 8 mm/s, at a load of 30 N and after 1,000 cycles.

9. The polymer composition that can be compounded or extruded into a polymer article as defined in claim 1, wherein the reinforcing fibers comprise glass fibers, the glass fibers being present in the polymer composition in an amount from about 10% to about 30% by weight.

10. The polymer composition that can be compounded or extruded into a polymer article as defined in claim 1, wherein the composition exhibits a Charpy notched impact strength of greater than 9 kJ/m² at 23° C.

11. An apparatus comprising:
a first sliding member in operative association with a second sliding member, the first sliding member and the second sliding member being configured to remain in contact and move relative to each other,
wherein the first sliding member and the second sliding member are both made from the polymer composition as defined in claim 1.

12. The apparatus as defined in claim 11, wherein the apparatus is a medical inhaler or injector.

13. A polymer composition that can be compounded or extruded into a polymer article comprising:
a polyester polymer, the polyester polymer comprising a polybutylene terephthalate, the polybutylene terephthalate polymer being present in the polymer composition in an amount greater than 60% by weight;
a masterbatch comprising a tribological modifier comprising an ultra-high molecular weight silicone having a kinematic viscosity of greater than 100,000 mm²s⁻¹ dispersed in a carrier polymer, the ultra-high molecular weight silicone being present in an amount of from about 0.1% to about 6% by weight based upon the weight of the polymer composition, the ultra-high molecular weight silicone being present in an amount of from about 10% to about 60% by weight based upon the weight of the combination of the ultra-high molecular weight silicone and the carrier polymer, and wherein the carrier polymer comprises a polyester elastomer; and
a second tribological modifier comprising a fluoropolymer powder having an average particle size of less than 15 microns and greater than 0.5 microns, the fluoropolymer powder having a melt flow rate of less than 3 g/10 min.

14. The polymer composition that can be compounded or extruded into a polymer article as defined in claim 13, wherein the second tribological modifier comprises a polytetrafluorethylene.

15. The polymer composition that can be compounded or extruded into a polymer article as defined in claim 13, wherein the ultra-high molecular weight silicone is a polydimethylsiloxane.

* * * * *